(12) United States Patent
Rada

(10) Patent No.: US 6,289,682 B1
(45) Date of Patent: *Sep. 18, 2001

(54) SPECIMEN PREPARATION APPARATUS

(76) Inventor: David C. Rada, P.O. Box 3826, Shawnee, KS (US) 66203

( * ) Notice: Subject to any disclaimer, the term of this patent is extended or adjusted under 35 U.S.C. 154(b) by 0 days.

This patent is subject to a terminal disclaimer.

(21) Appl. No.: 09/382,729

(22) Filed: Aug. 25, 1999

(51) Int. Cl.[7] .................................................... F25B 19/00

(52) U.S. Cl. ................................ 62/51.1; 62/320; 62/341; 83/374; 83/459; 83/915.5; 269/8

(58) Field of Search ............................ 62/51.1, 320, 341; 269/8; 83/459, 374, 915.5

(56) References Cited

U.S. PATENT DOCUMENTS

| | | | |
|---|---|---|---|
| 1,849,457 | * | 3/1932 | Johns ...................................... 62/341 |
| 1,924,225 | * | 8/1933 | Yamane .................................. 62/341 |
| 2,260,450 | * | 10/1941 | Guinane ................................. 62/341 |
| 3,209,821 | | 10/1965 | Zeytoonian . |
| 3,218,896 | | 11/1965 | McCormick . |
| 3,296,821 | | 1/1967 | Malinin . |
| 3,520,055 | | 7/1970 | Jannett . |
| 3,598,006 | | 8/1971 | Gerber . |
| 3,654,019 | | 4/1972 | Cusik . |
| 3,667,330 | | 6/1972 | Kobernick . |
| 3,713,304 | * | 1/1973 | Knutrud ................................. 62/341 |
| 3,737,335 | | 6/1973 | Feinberg . |
| 3,742,802 | | 7/1973 | Maerz . |
| 3,744,262 | | 7/1973 | Bose . |
| 3,765,289 | | 10/1973 | Gerber . |

(List continued on next page.)

OTHER PUBLICATIONS

Evaluation of a Method for Controlled Tissue Embedding for Histologic Evaluation of Tumor Margins; Daniel E. Gormley, M.D.; *The American Journal of Dermatopathology*; 9(4); 308–315, 1987.

Chemosurgical Reports: Frozen–Section Processing with the Miami Special; C. William Hanke, M.D. et al; *J. Dermatol. Surg. Oncol.* 9:4 Apr. 1983.

Mohs Surgery; Neil A. Swanson, M.D.; *Arch Dermatol*—vol. 119, Sep. 1983.

A New Method for Preparing Tissue Blocks for Cryostat Sectioning; Vernon H. Carter, M.D.; *J. Dermatol. Surg. Oncol.* 11:7 Jul. 1985.

How to Prepare Tissue Blocks; Justo Concepcion; (published as Letter to the Editor), *J. Dermatol. Surg. Oncol.* 12:2 Feb. 1986.

Technical Procedures for Mohs Fresh Surgery; Ana Maria Picoto Antonio Picoto, M.D.; *J. Dermatol. Surg. Oncol.* 12:2 Feb. 1986.

*Primary Examiner*—Ronald Capossela
(74) *Attorney, Agent, or Firm*—John C. McMahon

(57) ABSTRACT

An apparatus for forming an amorphous tissue specimen into a cooled block while preserving the anatomical orientation of the specimen includes a base assembly, a system of magnetic movable wall units and a cover which may be intercoupled to form an enclosed specimen cavity. The wall units each include a hinged panel at one end, so that the wall units may be adjustably intercoupled to form various planar surfaced shapes, such as a rhomboid or eccentric block form. Each wall unit also includes a reservoir for a refrigerant such as liquid nitrogen for cooling the enclosed specimen to an optimal temperature for tissue cutting. The base is equipped with orientation indicia and temperature sensors. A synthetic resin may be applied to the specimen-contacting surfaces of the form in order to facilitate release of the cooled specimen. The invention provides a greatly improved method for rapid harvesting of the entire margin surface area a tumor to allow medical personnel to determine if any malignant tumor cells exist on the specimen margins.

18 Claims, 5 Drawing Sheets

U.S. PATENT DOCUMENTS

| | | |
|---|---|---|
| 3,803,958 | 4/1974 | Fernandez-Moran . |
| 3,832,923 | 9/1974 | Lassmann et al. . |
| 3,948,061 | 4/1976 | Kidwell . |
| 4,012,475 | 3/1977 | Kindel . |
| 4,060,440 | 11/1977 | Behme . |
| 4,190,472 | 2/1980 | Slonicki . |
| 4,532,838 | 8/1985 | Söderkvist . |
| 4,543,862 | 10/1985 | Levene . |
| 4,545,831 | 10/1985 | Ornstein . |
| 4,553,406 | 11/1985 | Richelli et al. . |
| 4,695,339 | 9/1987 | Rada . |
| 4,751,828 | 6/1988 | Coulter et al. . |
| 4,752,347 | 6/1988 | Rada . |
| 5,103,651 * | 4/1992 | Coelho et al. ............ 62/341 |
| 5,168,726 | 12/1992 | York . |
| 5,321,955 * | 6/1994 | Leonard ................ 62/51.1 |
| 5,352,472 * | 10/1994 | Lucke ................... 62/341 |
| 5,829,256 * | 11/1998 | Rada .................... 62/51.1 |

\* cited by examiner

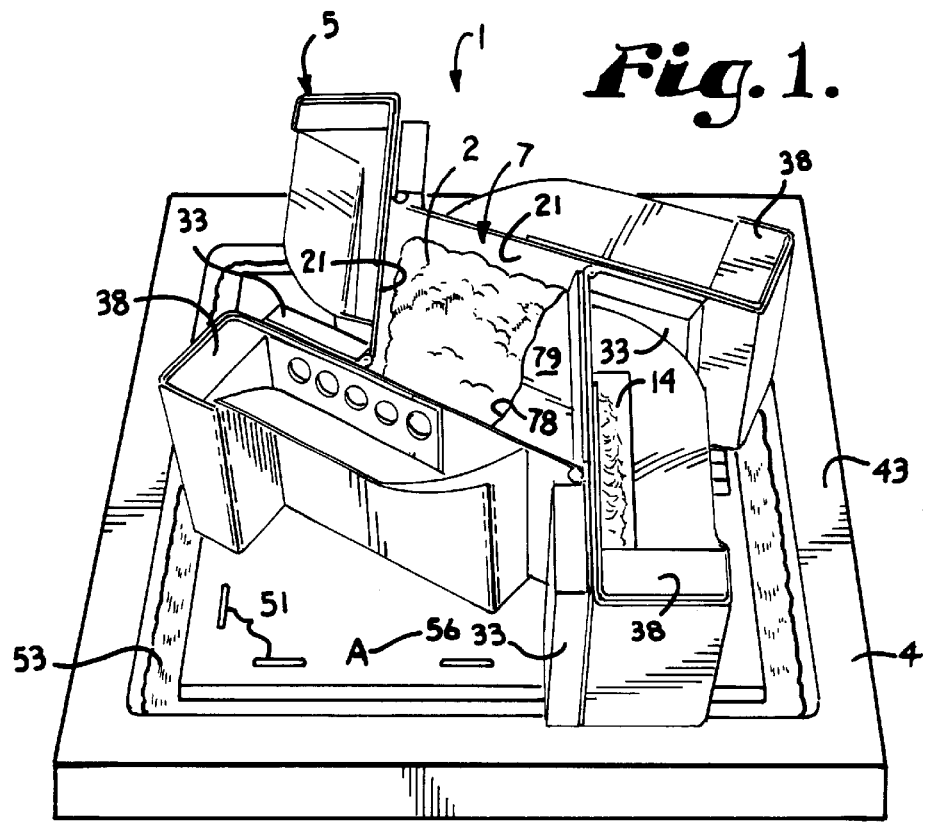
Fig.1.
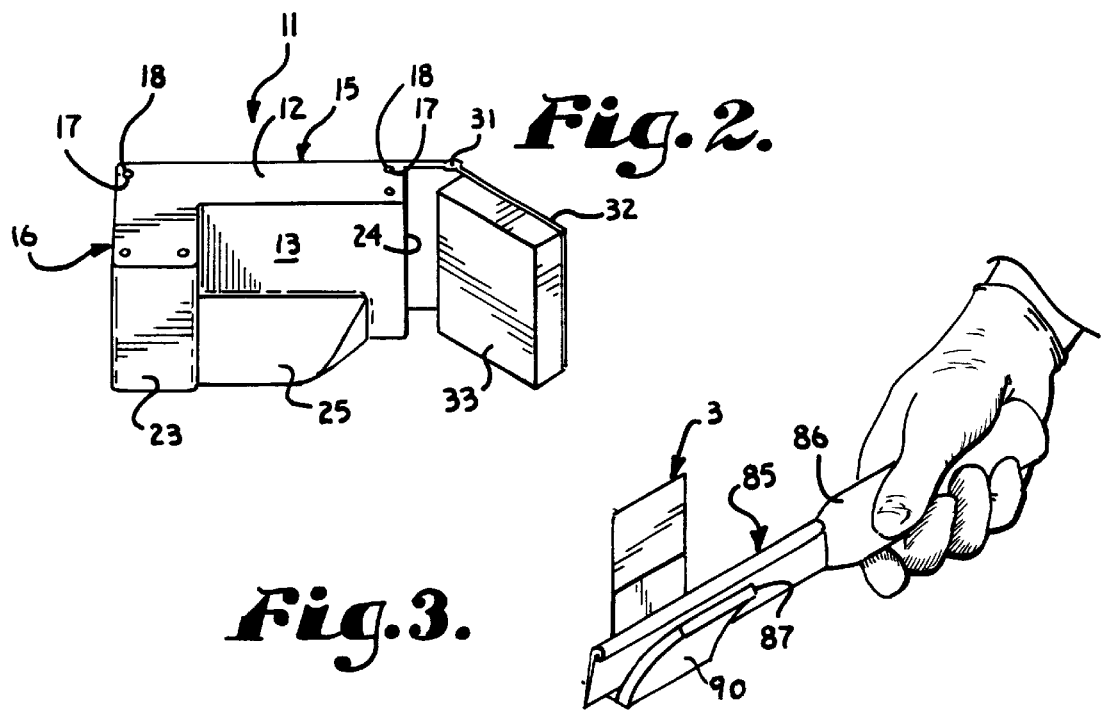
Fig.2.
Fig.3.

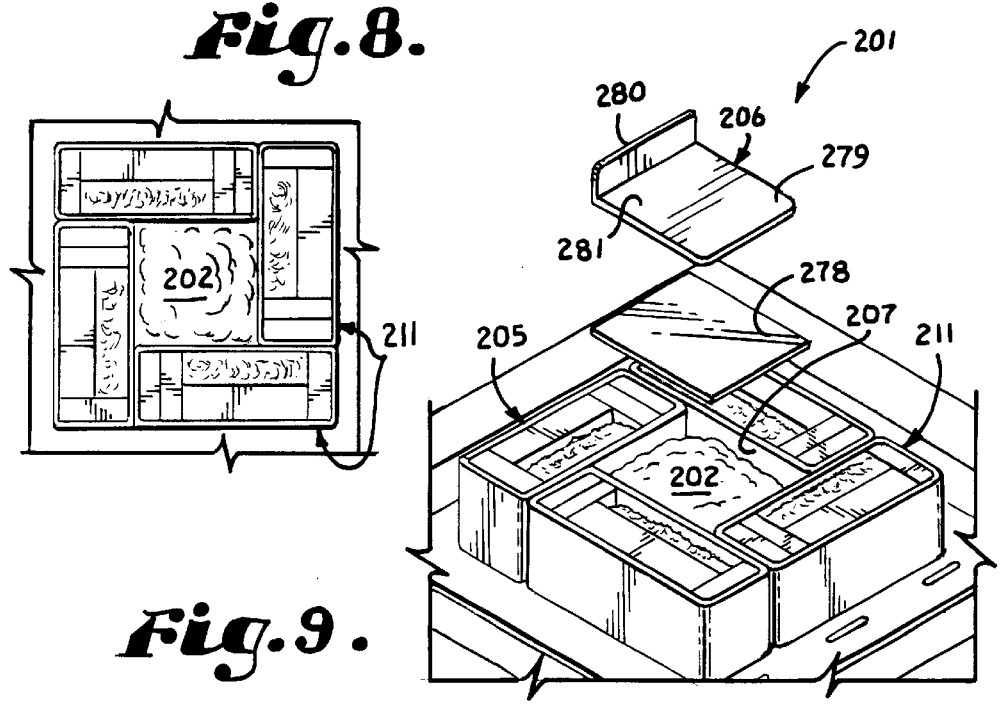
Fig.8.
Fig.9.
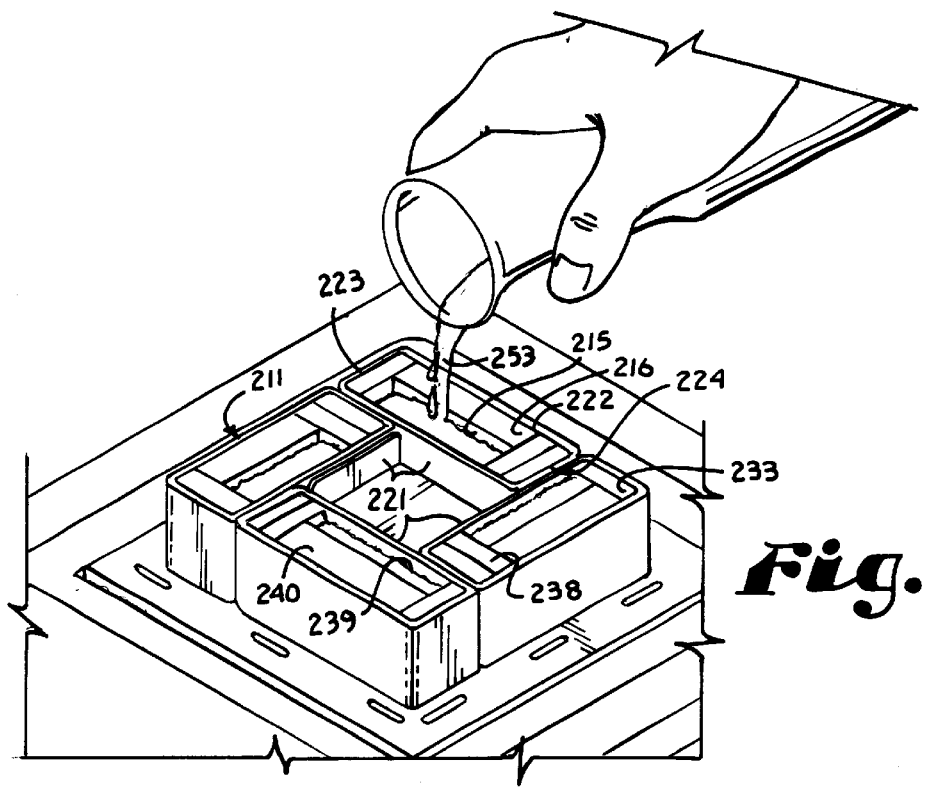
Fig.10.

SPECIMEN PREPARATION APPARATUS

BACKGROUND OF THE INVENTION

The present invention is broadly concerned with an apparatus and method for forming, quick freezing and harvesting tissue from the margins of a tumor specimen, while preserving the anatomical orientation of the specimen. More particularly, it is concerned with an apparatus having a base, movable walls and a cover which may be adjustably intercoupled to frame a form for receiving and shaping an amorphous tissue specimen into a planar-surfaced block. The device further includes structure for freezing the specimen to a predetermined optimum temperature, so that the specimen will retain its shape for cutting after the form is removed.

Biopsy, or surgical removal of a tissue specimen for histologic examination, is frequently employed in order to establish a precise diagnosis. When a lesion is known or suspected to be malignant, the entire mass is typically excised, if possible, and an examination technique is often employed in which the tumor margin surface area is examined. This technique involves microscopic screening of the exterior surface area of the tumor for the presence of malignant cells to ensure that all such cells have been removed. If practiced effectively, tumor margin surface area examination enhances the likelihood of complete removal of all cancerous cells of a localized malignancy. Where removal of the malignancy was not complete, the method may be used to precisely identify the location of any residual malignancy for subsequent removal or, where that is not possible, for radiation therapy.

Once harvested, the tissue is frozen using, for example, the methods and devices set forth in Applicant's previous U.S. Pat. Nos. 4,695,339; 4,752,347; 5,628,197; 5,829,256; and 6,094,923, which patents are incorporated herein by reference, and the tissue is then sectioned into thin layers. The tissue is preferably snap frozen at a controlled rate in order to obtain a high quality frozen section which is not marred by voids and artifacts which might impair examination and diagnosis. Following dissection from the tumor, the tissue margin surfaces may also be further examined by methods such as electron microscopy.

In order to be effective, the technique of tumor margin surface area examination must include microscopic examination of the entire surface margin of the excised tumor. Moreover, the anatomical orientation of the tissue must be maintained throughout the procedure so that the surgeon may return to a specific source area of the tumor margin surface in order to excise additional tissue until histologic examination indicates that only healthy cells remain.

One of the problems associated with preparation of specimens for this method of histologic examination is that the tissue is normally excised in irregular shapes. Many tumors, such as breast cancer, are amorphous because they are comprised of fatty tissue. Anatomical orientation of the specimen is difficult to maintain when sectioning such specimens that are obtained, for example, in a lumpectomy for breast cancer.

It is difficult to conduct a thorough examination of the tumor margin surfaces in all planes because of the irregular geometric shape of such tumors. For example, a thin, planar surface slice of a round mass only effects a very small area of the total surface. That is, each thin section obtained by conventional methods from a tumor mass reveals only a portion of the tumor margin. However, the number of sections which can be examined microscopically is limited by practical considerations, such as time and availability of equipment and it is very difficult to orientate the excision position from an area where a large number of specimens were obtained.

It is important that the histologic examination be performed quickly, since the patient must be kept under anesthesia pending the microscopic evaluation, in case any additional tissue must be excised. For this reason, it is normally not possible to process large numbers of tumor margin surface sections in an effort to perform a completely thorough pathologic examination.

In order to obtain slices from the entire tumor margin surface area, it has been found to be expedient to form the tissue specimen into a polyhedron block having plane surfaces. Harvesting of the tissue from all of the resulting planar surfaces of the block serves to ensure that the entire tumor margin surface area has been harvested for examination. Because the block presents a limited number of such plane surfaces (six), the procedure can be conducted fairly quickly.

While it is important to form the entire excised tumor mass into a block, not all tumor masses are of the same size or shape, and many do not present bilateral symmetry. Although some tumor masses can be formed into a cube-shaped block having right angles or a rhomboid block having opposed complementary acute and obtuse angles at the vertices, there is a need for a form which can be adjusted to accommodate eccentric masses, which may lack parallel sides and angular symmetry.

In order to speed the examination process, the specimen must be quickly frozen to a predetermined temperature which will permit the tissue to retain a structured form. The specimen must then be promptly released from the form for harvesting of the tumor margin surfaces.

The apparatus and method of the present invention are specifically designed to quickly form and freeze an amorphous or eccentric specimen into a shape having a limited number of planar surfaces which are easily sectioned for rapid microscopic evaluation of the entire tumor margin.

SUMMARY OF THE INVENTION

The present invention is directed to an apparatus and method for forming an amorphous tissue specimen into a chilled block with generally planar surfaces, while preserving the anatomical orientation of the specimen. The invention provides a greatly improved method for rapid harvesting of the entire margin surface area of a tumor. The apparatus has a base supporting a system of movable wall units that are at least partially magnetic and a cover which are intercoupled, especially by magnetic attraction, to form a horizontally enclosed specimen cavity. The wall units each include a hinged panel at one end, so that they may be adjustably magnetically intercoupled to form a rhomboid or eccentric block form. Each wall unit also includes a reservoir for a cryogenic, liquid such as liquid nitrogen, for cooling the enclosed specimen to an optimal temperature for tissue cutting. The base is equipped with orientation indicia and temperature sensors. A synthetic resin coating may be applied to the specimen-contacting surfaces of the form in order to facilitate release of the chilled specimen.

OBJECTS AND ADVANTAGES OF THE INVENTION

The principal objects of the present invention are to provide a method and apparatus for forming a tissue specimen; to provide such a method and apparatus for forming an amorphous tissue specimen into a tissue block having planar surfaces; to provide such a method and apparatus for forming a tissue block having a limited number of planar surfaces which may be easily and quickly sectioned by a knife or other cutting instrument; to provide such a method and apparatus which maintain the anatomical orientation of a tissue specimen obtained by surgical excision; to provide such a method and apparatus which quick freeze the specimen to a predetermined temperature; to provide such a method and apparatus which permit rapid harvesting of tissue from the entire margin surface area of a tumor; to provide such an apparatus having magnetic wall units which may be adjusted in relative position to form a tissue specimen into a block; to provide such an apparatus having a magnetic base for supporting magnetic wall units in place; to provide such an apparatus having hinged wall units; to provide such an apparatus wherein the wall units each include a reservoir for holding a cryogenic liquid; to provide such an apparatus including a temperature indicator device; to provide such an apparatus having a base including a trough for collecting excess cryogenic liquid; to provide such an apparatus having walls and a base coated with a non-stick or easy release coating; to provide a method for using such an apparatus to form a surgically excised tissue specimen into a block, while retaining its anatomical orientation, cooling the specimen to an optimal freezing temperature, releasing the specimen, cutting a slice from each of the planar surfaces of the block, microscopically examining the slices for malignant cells, and excising additional specimens from a patient; providing such an apparatus and method which are relatively easy to use, inexpensive to produce and particularly well-suited for their intended usage.

Other objects and advantages of this invention will become apparent from the following description taken in conjunction with the accompanying drawings wherein are set forth, by way of illustration and example, certain embodiments of the invention.

The drawings constitute a part of this specification and include exemplary embodiments of the present invention and illustrate various objects and features thereof.

BRIEF DESCRIPTION OF THE DRAWINGS

FIG. 1 is a perspective view of a specimen preparation apparatus in accordance with the present invention, showing a tissue specimen in place with the cover unit removed.

FIG. 2 is a perspective view of a single wall unit of the specimen preparation apparatus, illustrating a hinged panel in an extended position.

FIG. 3 is a perspective view of a partial frozen tissue block formed in the apparatus of FIG. 6, and illustrating harvesting of a formed, planar tissue margin surface by slicing with a heated knife.

FIG. 8 is a top plan view of the apparatus of FIG. 6, illustrating the wall units in a tissue receiving configuration and engaging the surfaces of a tissue specimen.

FIG. 9 is a partially exploded perspective view of the apparatus of FIG. 6, illustrating a specimen cover unit.

FIG. 10 is a perspective view of the apparatus of FIG. 6, illustrating a tissue specimen engaged in a specimen compartment and an operator pouring liquid nitrogen onto the apparatus to cool the specimen.

DETAILED DESCRIPTION OF THE INVENTION

Figure 4:
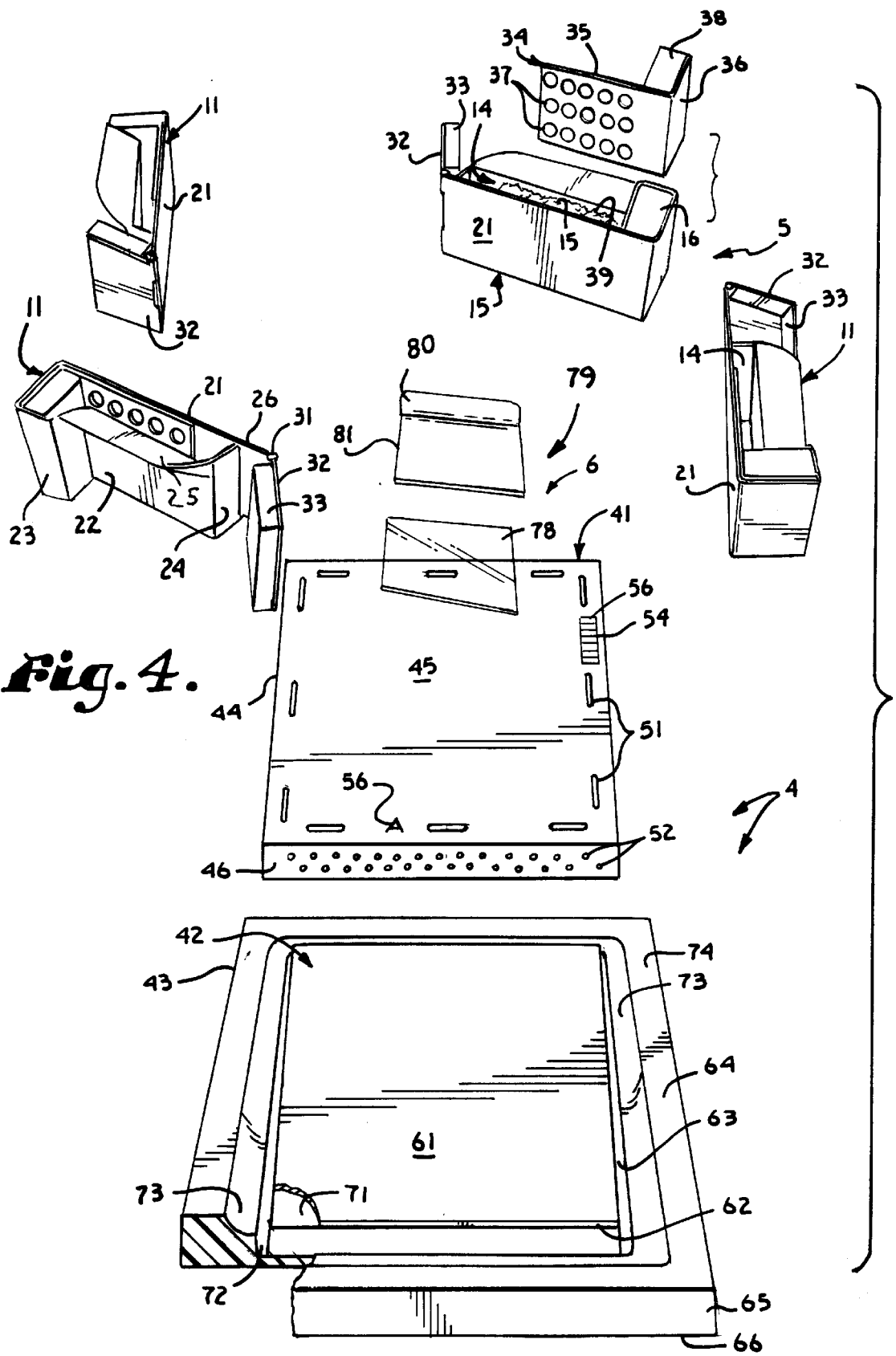
FIG. 4 is an exploded perspective view of the apparatus of FIG. 1, including multiple wall units having hinged panels and showing a magnetic insert removed from a reservoir of one of the wall units, the cover unit, a base platform, a base plate and a tray with portions removed to show detail thereof.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

I. Variable Shape Specimen Block-Forming Apparatus

Referring now to the drawing, a specimen preparation apparatus 1 for forming a tissue specimen 2 into various planar sided shapes such as the illustrated rhomboid or diamond shaped block 3 in accordance with the invention broadly includes a base assembly 4 supporting a form assembly 5 and a cover unit 6. Each of these elements is constructed so that when intercoupled, they cooperatively define a generally enclosed, specimen-receiving compartment 7 having planar surfaces for engaging the outer surface of a spherical or odd shaped specimen 2 and forming the specimen into a block 3 with planar sides. The resulting block 3 is often rectangular or square in cross section; however, the block 3 may have other shapes including, but not limited to, shapes having a diamond, trapezoidal, triangular or other polyhedral cross section. The shape of the form assembly 5 may be adjusted to accommodate tissue specimens of elongate or eccentric shape and to form specimens into an irregular polyhedron block 3.

In more detail, the form assembly 5 includes wall units 11, see FIG. 2 where a wall unit 11 is shown inverted, each having a generally L-shaped planar bottom wall 12 coupled with a relatively thin sidewall 13 extending perpendicularly from the edge of the bottom wall and circumscribing an interior reservoir 14, having an elongate back portion 15 and a shorter, transversely extending leg portion 16. The bottom wall 12 includes spaced indents 17 for receiving synthetic resin guides 18, to facilitate movement of the wall units 11 over the base 4 and to prevent scratches which might result in adherence of the tissue specimen 2 to the surface of the base 4.

Each unit sidewall 13 includes an elongate back wall 21, a generally dog-leg shaped front wall 22 which is slightly shorter in length than the back wall 21, a first end wall 23 and a second end wall 24. The upper portion of the front wall 22 flares outwardly to form a lip 25. Because of the difference in length between the back wall 21 and front wall 22, the back wall 21 extends beyond the short end wall 23 so as to form a planar flange 26. A hinge 31 intercouples the flange 26 with a rotatable panel 32 that is adjustable and rotatable about the hinge 31 to join with the flange 26 at an infinite number of angles. The second end wall-facing surface of the panel 32 is coupled with a magnet 33 positioned on one side thereof.

A generally L-shaped magnet cage 34 (see FIG. 4) is positioned in each unit reservoir 14 and has a back 35 coupled with a perpendicularly extending leg 36, the back including a plurality of spaced apertures 37. The cage leg 36 is coupled with a magnet 38 positioned on one side thereof. The cage 34 is designed for registry with the reservoir 14, so that, when in place, the magnet 38 is positioned in the reservoir leg portion 16, and the back 35 rests against the reservoir back wall 21. The remainder of the reservoir back portion 15 which is not occupied by the cage back 35 may be doped or filed with cotton 39 or other suitable dampering material.

Magnets 33 and 38 are employed to selectively magnetically join or couple the wall units 11 in backward facing relationship in an infinite number of positional relationships. The magnets 33 and 38 also hold the units 11 in place so that back walls 21 and panels 32 cooperatively frame a form assembly 5 which is horizontally adjustable along multiple axes. The illustrated magnets 33 and 38 are generally square in shape although it is foreseen that many shapes may be used in accordance with this invention. Magnets 33 and 38 are permanent and may be constructed of any suitable magnetic material.

As best shown in FIGS. 1 and 4, in use the wall units 11 are joined in a selected configuration best suited to form the basic tissue sample 2 into the desired block 3. The intercoupled wall units 11 are supported by a base 4, having a platform 41, a base plate 42 and an overflow tray 43. The platform 41 has a planar deck 44 presenting an upper surface 45 that is supported by dependent sidewalls 46. The deck 44 includes a plurality of peripherally spaced slots 51, and the sidewall 46 includes a pattern of spaced apertures 52. As will be discussed later, cryogenic liquid is used to cool the apparatus 1 and the slots 51 and apertures permit excess cryogenic liquid 53 flowing away from the form assembly 5, to pass downwardly to collect in the overflow tray 43. The platform upper surface 45 includes a recess 54 for receiving a temperature sensitive indicator strip 55, and specimen orientation indicia 56. The indicia 56 may be stamped, engraved or printed onto the surface 45. Alternatively, it is foreseen that a movable tag bearing the indicia 56 may be placed on the surface 45 and held in place by a magnet, or other suitable means.

The platform 41 surmounts an imperforate planar base plate 42, presenting upper and lower surfaces 61 and 62 and a perimeter margin 63. The plate 42 is sized for registry with the platform 41, so that the deck 44 rests upon the plate upper surface 61 and the plate perimeter margin 63 fits within the circumscribing sidewalls 46 of the platform 41.

Except for the panels 32, the wall units 11 and base platform 41 are preferably constructed of aluminum or other material having a high coefficient of thermal conductivity. The panels 32, magnet cage 34 and base plate 42 are constructed of a magnetic stainless steel alloy or other suitable material which is subject to the attractive forces of magnets 33 and 38.

The platform-surmounted plate 42 is supported by a tray 43, having an upper surface 64, four side walls 65, and a lower surface 66. The upper surface 64 includes a planar central portion 71 bounded by a narrow recess 72, configured to receive the dependent platform sidewalls 46. The outer perimeter of the recess 72 is bounded by a substantially wider, shallow trough 73 for receiving any overflowing cryogenic liquid 53. The tray 43 includes a planar margin surface 74 circumscribing the outer perimeter of the trough 73. The tray 43 is preferably constructed of a synthetic resin or plastic, such as polyvinyl chloride or other suitable material.

A cover unit 6 includes a specimen cover 78 and a cover plate 79. The specimen cover 78 is preferably constructed of a transparent synthetic resin material or plastic which may be trimmed to fit the surface dimensions of the desired shape of the specimen compartment 7. The cover plate 79 is generally L-shaped, having a collar portion 80 and a planar portion 81. The cover plate 79 is constructed of a magnetizable material, such as a magnetizable stainless steel alloy, so that attraction of the collar portion 80 to the form assembly magnets 33 and 38, holds the cover plate 79 in place surmounting the specimen cover 78.

An excised tissue specimen 2 is generally amorphous in shape, although it may be regular or irregular. The base platform 41, wall units 11 and cover plate 79 cooperatively form a specimen-receiving compartment 7 that is selected to best fit the specimen 2 and form it into the block 3 having planar walls. While the purpose of the compartment 7 is to form the specimen 2 into a solid polyhedron block having plane faces, the shape of the compartment 7 may be adjusted to conform generally with that of the specimen 2. If the specimen is elongate or otherwise eccentric, an irregular polyhedron having incongruent plane faces may be formed by manipulation of one or more of the magnetic wall units 11.

The specimen preparation apparatus is used in association with a knife 85, depicted in FIG. 3. The knife 85 is preferably a hand-held thermocutter, having a handle 86 and a generally straight blade 87. The handle 86 incorporates a transformer which heats the blade 87. The handle 86 may also include a temperature controller as well as a switch.

In use, a surgeon excises a tissue specimen 2 to be prepared for tumor margin surface area examination and places it in the approximate center of the base platform upper surface 45 so that the anatomical orientation of the specimen 2 corresponds to the platform orientation indicia 56. An operator places three or more wall units 11 in upstanding position on the base platform surface 45 with the back wall surfaces 21 facing the specimen 2 and the panels 32 in closed position with the magnet 33 resting adjacent the flange 26. The operator urges the wall units 11 toward the specimen 2 in order to approximate the overall shape of the specimen 2 and continues convergent movement of the units 11 until the back wall surfaces 21 engage the tissue specimen 2 with sufficient force to conform the generally curvate surfaces of the specimen 2 to the planar wall surfaces 21. In order to hold the wall units 11 in place against the tissue specimen 2, the panels 32 are rotated about the hinges 31 so that each magnet 33 is attracted through back wall 21 to either a cage back 35 or another magnet 38. In addition, the attractive forces of magnets 33 and 38 to the base plate 42 serve to maintain the form assembly 5 in place on the base 4.

The operator trims the cover 78 to the surface dimensions of the specimen compartment 7, and places it atop the specimen 2. The operator installs the cover plate 79 over the specimen cover 78, pushing it downwardly so that the cover 78 engages the tissue specimen 2 with sufficient force to conform the generally curvate surfaces of the specimen 2 to the planar cover surface 78. The position of the cover plate 79 is maintained by attraction of the collar 80 to one or more of the magnets 33 and 38.

Once the tissue specimen 2 is engaged by the surfaces of the specimen compartment 7, an operator pours a cryogenic liquid, such as liquid nitrogen 53, over the lip 25 and into each reservoir unit 14, pouring additional liquid nitrogen over the specimen compartment cover plate 79. The liquid nitrogen 53 flows through cage apertures 37 to cool the specimen-contacting back walls 21. Some liquid nitrogen flows out of the specimen compartment 7 at the joints between wall units 11 and flows through platform slots 51 and apertures 52 to partially fill the tray recess 72. Any excess cryogenic liquid 53 overflows the recess 72 and is collected in the trough 73.

The operator monitors the temperature indicator strip 55, and when a predetermined, optimum temperature for tissue cutting is reached, the operator disengages the cover plate 79, specimen cover 78 and wall units 11 to release the frozen specimen. In order to facilitate release of the specimen block 3, the operator may remove the liquid nitrogen from the reservoirs 14 by lifting the unit from the tray and pouring off the cryogenic liquid 53, or by use of an automatic pipette or other similar means.

Those skilled in the art will appreciate that the reservoir rear walls 21 may be equipped with heating elements which may be actuated to facilitate release of the specimen block 3. Alternatively, the operator may apply heat from an external source to the walls 21 using a wand.

Once the form assembly 5 and cover unit 6 are removed, the block 3 may be removed from the base assembly 4 for harvesting of the planar tissue surfaces. In preferred embodiments a thermal knife 85 is employed to quickly cut through the frozen tissue. The tissue margin surfaces, such as cut specimen surface 90, are labeled, mounted on object holders and thin-sectioned on a microtome, such as a cryostat for viewing under a microscope.

If malignant cells are observed on one or more of the tissue margin surfaces, the anatomical orientation is noted, and an additional specimen is surgically excised from the corresponding location, and the process is repeated until all possible malignant cells are removed. If additional excision is not possible, the anatomical orientation of the residual malignancy is recorded for use in radiation therapy.

II. Apparatus With High Gauss Permanent Magnet

Figure 5:
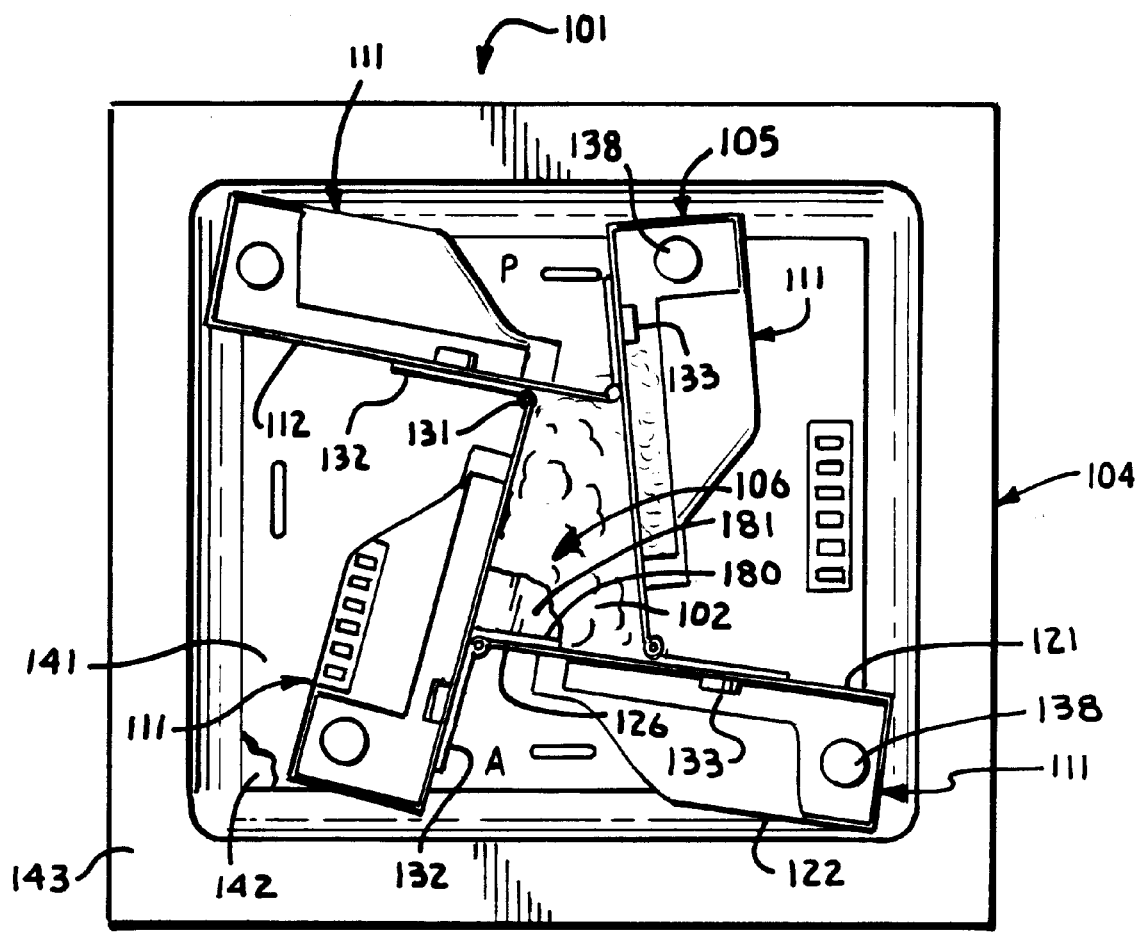
FIG. 5 is a top plan view of a second embodiment of the apparatus of FIG. 1, illustrating the use of high-Gauss permanent magnet.
Figure 6:
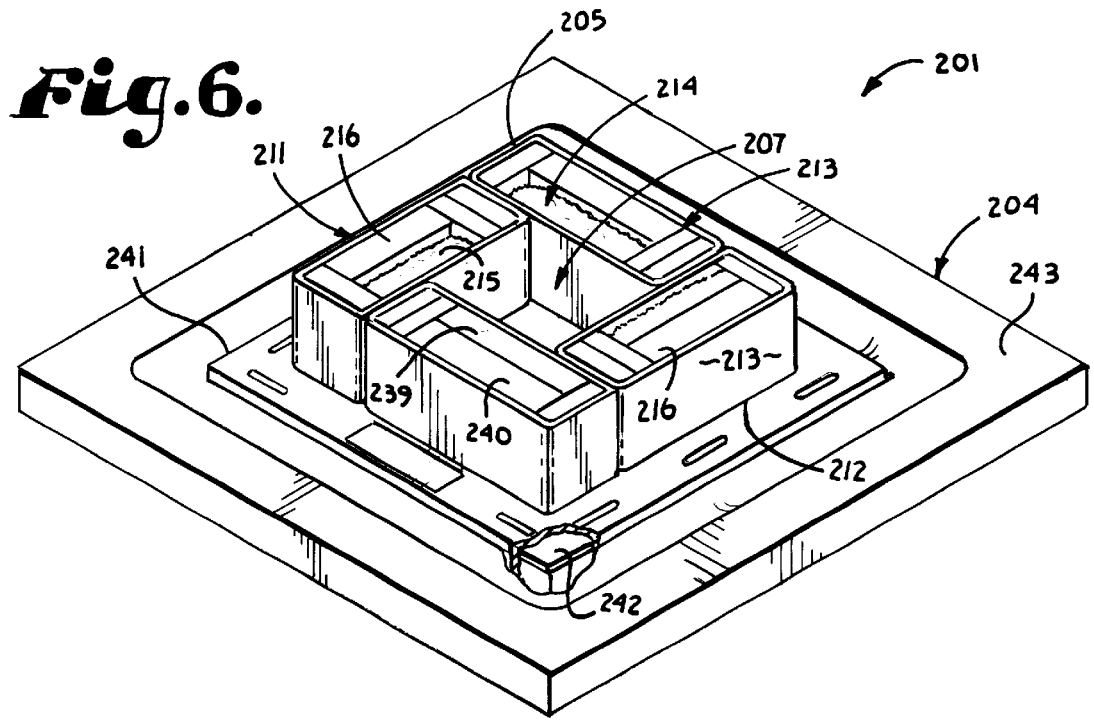
FIG. 6 is a perspective view of a third embodiment of a specimen preparation apparatus employed for forming a rectangular or cube-shaped block of tissue.
Figure 7:
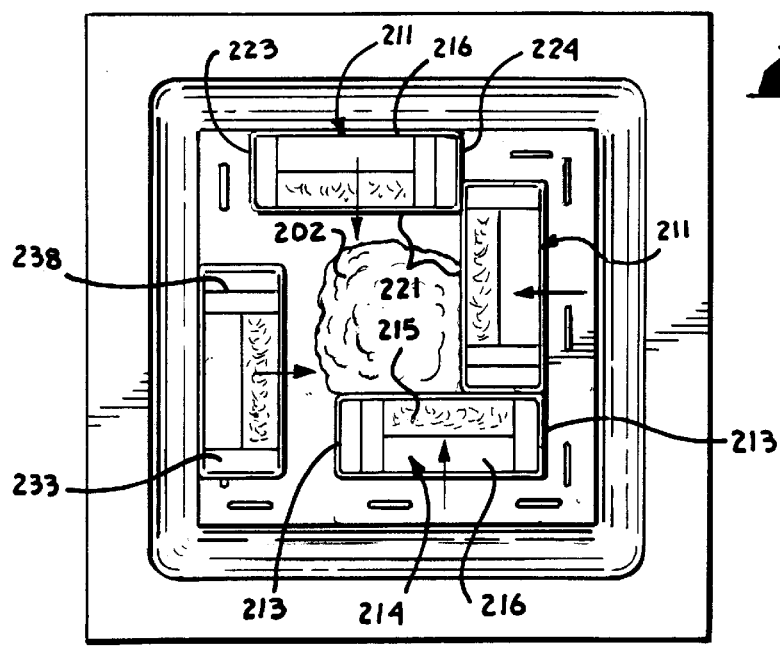
FIG. 7 is a top plan view of the apparatus of FIG. 6, illustrating a tissue specimen in place in the apparatus and depicting movement of the wall units into position surrounding the specimen.

As best shown in FIG. 5, a second embodiment of a specimen preparation apparatus 101 for forming a tissue specimen 102 is illustrated. The structure of this embodiment is substantially identical to that previously described, except that high-powered magnets are employed, obviating the need for the larger magnets and magnetically attractive magnet cages previously described.

The specimen preparation apparatus 101 includes a base assembly 104 supporting a form assembly 105, and cover unit 106. A specimen receiving compartment 107 is cooperatively formed by the magnetic coupling of wall units 111, each having a bottom wall 112, coupled with a sidewall 113 circumscribing an interior reservoir 114, having an elongate back portion 115 and a shorter, leg portion 116. The wall units 11 in FIG. 5 are joined to form a block 102 with a trapezoidal cross section.

The sidewall 113 includes a back wall 121, extending beyond a front wall 122 in a planar flange 126, first and second end walls 123 and 124, and a hinge 131 coupling the flange 126 with a panel 132. A pair of magnets 133 and 138 is employed to couple the wall units 111 in backward-facing relationship. The magnets 133 and 138 are generally disk-shaped and are constructed of a particularly high Gauss material. Rare earth permanent magnet compounds such as, for example, neodymium-iron-boron are particularly preferred. Because of their strength, magnets 133 and 138 are substantially smaller in size than the panels 132, and are generally disk-shaped.

The intercoupled wall units 111 are supported by a base assembly 104, having a platform 141, base plate 142 and base tray 143. A cover unit 106 includes a specimen cover 178 and a cover plate 179 that is magnetically attractable and having a collar portion 180 and a planar portion 181.

In use, three or more wall units 111 are positioned on the base platform 141, with the back wall surfaces 121 facing a tissue specimen 102. Magnets 138 are placed in reservoir legs 116 in contact with the bottom wall 112, and are magnetically attracted to the base plate 142. Each panel 132 is rotated about hinge 131 until it contacts an adjacent back wall 121. The operator positions a magnet 133 at a location on the inside surface of the reservoir back wall 121 so that the magnet 133 is attracted to the panel 132. The operator installs the cover plate 179 over the specimen cover 178. The operator may adjust the location of a magnet 133, if necessary, so that attraction of the magnets 133 to the collar 180 holds the cover plate 179 in place.

Those skilled in the art will appreciate that tissue specimen 102 may be conformed to the back wall surfaces 121 until it completely fills the specimen compartment 107 to the upper margins of the walls 121. In that case, the cover plate planar surface 181 may held in place atop the wall units 111 by one or more additional magnets (not shown) placed atop the planar portion 181 in magnetic attraction with one or more magnets 133 or top margins of panels 132.

III. Cube-Forming Apparatus

FIGS. 6–10 depict a third alternate embodiment of a specimen preparation apparatus 201, suitable for use to form a generally regular tissue specimen 202 into a polyhedron block having a 90° angle at each of the vertices, such as a cube or other solid with a generally rectangular cross section.

In more detail, the specimen preparation apparatus 201 includes a base assembly 204 supporting a form assembly 205 and cover unit 206. A specimen receiving compartment 207 is cooperatively formed by four magnetically coupled wall units 211, each having a generally rectangular bottom wall 212 orthogonally coupled with a sidewall 213 circumscribing an interior reservoir 214, having a back portion 215 and a front portion 216.

The sidewall 213 includes generally rectangular back and front walls 221 and 222, and a pair of generally square end walls 223 and 224. The endwalls 223 and 224 are coupled with one or more generally square-shaped magnets 233 and 238. Either or both of the magnets 233 and 238 may have multiple individual magnetic units. A generally rectangular spacer unit 240 of a synthetic resin material occupies the reservoir front portion 216, and the remaining reservoir back portion 215 is filled with cotton 239 or other suitable dampering substance adapted to receive cryogenic fluid. The magnets 233 and 238 are employed to couple the wall units 211 in generally end to side relationship and to maintain the wall units 211 in place to frame a form assembly 205, which is adjustable along the X and Y axes.

The intercoupled wall units 211 are supported by a base assembly 204 having a base plate 242 and base tray 243. A cover unit 206 includes a specimen cover 278 and a magnetizable cover plate 279, having a collar portion 280 and a planar portion 281.

In use, the form assembly 205 operates much as previously described. A surgeon excises a tissue specimen 202, having an irregular curvate surface. The specimen is placed on the base platform 241, and four wall units 211 are positioned on the platform 241, with the back wall surfaces 221 facing the specimen 202. An operator moves the wall units 211 along the X and Y axes to converge toward and exert force on the specimen 202 until the reservoir back wall surfaces 221 engage the curvate surfaces of the tissue specimen 202 and reform the tissue into a block with generally planar surfaces. The wall units 211 are held in place by the attraction of magnets 233 to magnets 238, and by the attraction of all of the magnets to the base plate 242. The operator trims the specimen cover 278 to fit and installs it in contact with the upper surface of the specimen 202. The cover plate 279 is then installed over the specimen cover, forming the specimen into a six-sided block. The cover unit 206 is held in place by attraction of magnets 238 to the collar portion 280. The operator pours a cryogenic liquid 253 into reservoir back portions 215 to chill the specimen 202.

It is understood that while certain forms of the present invention have been illustrated and described herein, it is not to be limited to the specific forms or arrangements of parts described and shows.

What is claimed and desired to be secured by Letters Patent is as follows:

1. An apparatus for preparing a tissue specimen for examination of the margin surfaces thereof; said apparatus comprising:
   a) a base having a surface thereon for receiving a tissue specimen;
   b) a plurality of movable wall units supported on said base, each wall unit having a specimen engaging surface;
   c) said wall units and said base being operably and adjustably intercoupled for cooperatively defining an enclosure for engaging and forming the specimen placed on said base surface into a plane-surfaced block; and
   d) each of said wall units including a reservoir for receiving a quantity of a cryogenic liquid for cryogenic cooling of the formed specimen and openings for placing cryogenic liquid into each respective reservoir.

2. The apparatus according to claim 1 including:
   a) a cover cooperating with said wall units and adapted to be placed in a covering portion over a specimen.

3. The apparatus according to claim 2, wherein said cover includes:
   a) a generally planar specimen engaging surface coupled with a magnetizable collar for receiving a magnetic force from one of said wall unit magnets for maintaining said surface in position engaging an upper surface of the specimen.

4. The apparatus according to claim 2, wherein:
   a) said enclosure circumscribes a cube shape.

5. The apparatus according to claim 2, wherein:
   a) said enclosure circumscribes an irregular polyhedron shape.

6. The apparatus according to claim 2, wherein:
   a) said base, wall units and cover include a non-stick coating for facilitating release of the specimen contacting the surfaces thereof.

7. The apparatus according to claim 1, wherein:
   a) said base is constructed of a magnetic material.

8. The apparatus according to claim 1, wherein said base further includes:
   a) anatomical orientation indicia for orienting the placement of the specimen thereon.

9. The apparatus according to claim 1, wherein:
   a) said base includes a thermometer.

10. The apparatus according to claim 1, wherein each of said wall units further includes:
    a) a generally planar surfaced member having pair of opposed ends; and
    b) a magnet associated with each of the ends for operably exerting a force to magnetically intercoupled said wall units.

11. The apparatus according to claim 1, wherein each of said wall units further includes:
    a) a generally planar surfaced member having first and second opposed ends;
    b) a first magnet coupled with said first end;
    c) a hinge rotatably intercoupling a second magnet with said second end; and
    d) said first and second magnets exerting forces magnetically intercoupling said wall units in spatially adjustable relationship.

12. The apparatus according to claim 11, wherein:
    a) a panel is coupled with said second magnet in supporting relationship.

13. The apparatus according to claim 1, wherein:
    a) said reservoir includes a lip.

14. The apparatus according to claim 1, wherein:
    a) said reservoir includes a quantity of a material adapted to damper a cryogenic liquid poured into said reservoir.

15. In an apparatus for preparing a tissue specimen, wherein the apparatus includes a base, a plurality of wall units and a cover, the improvement comprising:
    a) said wall units are moveable and each have an upstanding member with first and second opposed ends and a hinge coupled with said second end;
    b) a first magnet coupled with said first end and a second magnet rotatably coupled by said hinge to a remainder of said wall unit for adjustable movement of said second magnet relative to said wall member;
    c) said first and second magnets exerting forces to operatively provide for magnetic intercoupling of said wall units and said base to cooperatively define an adjustable compartment for receiving and forming the specimen into a planar surfaced block; and
    d) a freezing apparatus operably joined to said wall units and operably freezing the specimen after forming by said compartment.

16. The apparatus according to claim 15, wherein:
    a) each of said wall units includes a reservoir for receiving a quantity of a cryogenic liquid for cryogenic cooling of the formed specimen.

17. The apparatus according to claim 15, wherein said base is constructed of a magnetic material.

18. The apparatus according to claim 15, wherein:
    a) said base includes a thermometer.

* * * * *